United States Patent
Sun et al.

(10) Patent No.: US 6,667,406 B1
(45) Date of Patent: Dec. 23, 2003

(54) METHODS FOR THE SYNTHESIS OF COMPLEX REDUCED ISOINDOLE, ISOOXYINDOLE AND ISOOXYQUINOLINE LIBRARIES

(75) Inventors: Sengen Sun, San Diego, CA (US); William V. Murray, Belle Mead, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/520,323

(22) Filed: Mar. 7, 2000

Related U.S. Application Data

(60) Provisional application No. 60/123,645, filed on Mar. 10, 1999.

(51) Int. Cl.$^7$ .................. C07D 209/04; C07D 209/46; C07C 233/00; G01N 33/53; G01N 33/545
(52) U.S. Cl. .............. 548/508; 435/7.1; 435/DIG. 49; 436/531; 548/472; 548/491; 564/189; 564/204
(58) Field of Search ................ 435/7.1, DIG. 49; 436/531; 548/472, 491, 508; 564/189, 204

(56) References Cited

U.S. PATENT DOCUMENTS 6,018,054 A * 1/2000 Philipps et al. ............. 548/430

OTHER PUBLICATIONS

Brettle et al. J. Chem. Soc. Perkin Trans. I, 1983, pp. 387–394.*
Yedidia et al. Regioselectivity in Cycloaddition Reactions on Solid Phases. Can. J. Chem., vol. 58, Jun. 1980, pp. 1144–1150.*
Heerding et al. Combinatorial Chemistry. Use of an Intramolecular . . . to Construct Functionalized Hexahydroisoindoles. Tet. Lett., vol. 39, No. 38, Sep. 1998, pp. 6815–6818.*
Hermkens et al. Solid–Phase Reactions II. A Review of the Literature Nov. 95–Nov. 96, Tetrahedron, vol. 53, Apr. 1997, pp. 5643–5678.*
Kendall N. Houk, Javier Gonzalez and YiLi, Pericyclic Reaction Transition States: Passions and Punctilios, 1935–1995, Acc. Chem. Res. 1995, 28, 81–90 .
Arnold J. Gutierrez, Kenneth J. Shea and John J. Svoboda, The Intramolecular Diels–Alder Cycloaddition of N–Dienoyl Acrylimidates. An Efficient Approach for the Synthesis of Hexahydroisoquinolones and Hexahydroisoindolones, J. Org. Chem. 1989, 54, 4335–4344.
Toshio Moriwake, shin–ich Hamano, Seiki Saito, Shigeru Torii and Setsuo Kashino, Synthesis of the Chiral (8S)—7–AZA–1,3 (E), 9–Decatriene System from Natural α–Amino Acids an its Intramolecular Diels–Alder Reaction Directed Toward Chiral Trans–Hydroisoquinolones, J. Org. Chem. 1989, 54, 4114–4120.

A. Guy, M. Lemaire, M. Negre and J.P. Guette, Stereoselectivity in Intramolecular Diels Alder Reactions I : Synthesis of Hydroisoindoles, Tetrahedron Letters, vol. 26, No. 30, PP 3575–3578, 1985.
R.B. Woodward and Thomas J. Katz, The Mechanism of the Diels–Alder Reaction, Tetrahedron, 1959, vol. 5.pp. 70–89, Pergamon Press Ltd.
Achintya K. Sinhababu and Ronald T. Borchardt, Selective Ring C–Methylation of Hydroxybenzaldehydes via Their Mannich Bases, Synthetic Communications, 13(8), 677–683 (1983).
Peter V. Alston and Donald D. Shillady, A Reexamination of the Origin of Regioselectivity in the Dimerization of Acrolein. A Frontier Orbital Approach, J. Org. Chem., vol. 39, No. 23,1974.
Gottfried Brieger and Janet N. Bennett, The Intramolecular Diels–Alder Reaction, Chem. Rev. 1980, 80,63–97.
Dale L. Boger, Diels–Alder Reactions of Heterocyclic Azadienes; Scope and Applications, Chem Rev.1986,86, 781–793.
Henri B. Kagan and Olivier Riant, Catalytic Asymmetric Diels–Alder Reactions, Chem. Rev. 1992,92,1007–1–19.
Dale L. Boger, Azadiene Diels–Alder Reactions;Scope and Applications. Total Synthesis of Natural and Ent–Fredericamycin A, J. Heterocyclic Chem., 33,1519–1531 (1996).
Robert K. Boeckman, Jr. and Donald M. Demko, Stereocontrol in the Intramolecular Diels–Alder Reaction. 4. A Remarkable Effect of Overlap Reqirements in the Connecting Chain, J. Org. Chem. 1982,47,1789–1792.
Stephen F. Martin, Sidney A. Williamson, R.P. Gist and Karl M. Smith, Aspects of the Intramolecular Diels–Alder Reactions of Some 1,3,9–Trienic Amides, Amines, and Esters. An 1983,48,5170–5180.
Ernst Eibler, Peter Hocht, Bernhard Prantl, Henry Robmaier, Hans Markus Schuhbauer, Hubert Wiest and Jurgen Sauer, Transitions of Electron Demand in Pericyclic Reations: Normal, Neutral, and Inverse Diels–Alder Reactions of Polyhalogenated Cyclopentadienes, Liebigs Ann./Recueil 1997, 2471–2484.
Robert S. Atkinson, Stereoselective Synthesis, Science QD 481.A79 1995, pp. 156–181.

* cited by examiner

*Primary Examiner*—Maurie Garcia Baker

(57) ABSTRACT

Disclosed are methods of synthesizing libraries of diverse complex hexahydroisoindole, hexahydroisooxyindole and octahydroisooxyquinoline compounds through the use of a facile intramolecular Diels Alder reaction. The invention is further directed to methods for synthesizing the libraries on solid supports. The invention is further directed to methods for identifying and isolating such hexahydroisoindole, hexahydroisooxyindole and octahydroisooxyquinoline compounds with useful and diverse activities from such libraries.

8 Claims, No Drawings

US 6,667,406 B1

METHODS FOR THE SYNTHESIS OF COMPLEX REDUCED ISOINDOLE, ISOOXYINDOLE AND ISOOXYQUINOLINE LIBRARIES

This application claims the benefit under 35 U.S.C. §119(e) of prior application Ser. No. 60/123,645, filed Mar. 10, 1999.

BACKGROUND OF THE INVENTION

1. Field of the Invention

This invention is directed to methods of synthesizing libraries of diverse complex isoindole and isoquinoline compounds through the use of a facile intramolecular Diels Alder reaction. The invention is further directed to methods for synthesizing the libraries on solid supports. The invention is further directed to methods for identifying and isolating isoindole and isoquinoline compounds with useful and diverse activities from such libraries.

2. Background

Compounds having biological activity can be identified by screening diverse collections of compounds (i.e., libraries of compounds) produced through molecular biology techniques or synthetic chemical techniques. Such screening methods include methods wherein each member of the library is tagged with a unique identifier tag to facilitate identification of compounds having biological activity or where the library comprises a plurality of compounds synthesized at specific locations on the surface of a solid substrate wherein a receptor is appropriately labeled to identify binding to the compound, e.g., fluorescent or radioactive labels. Correlation of the labeled receptor bound to the substrate with its location on the substrate identifies the binding compound. Using these techniques, the development of efficient high throughput screening has greatly enhanced the pharmaceutical industry's ability to screen large numbers of compounds for biological activity.

Central to these methods is the screening of a multiplicity of compounds in the library and the ability to identify the structures of the compounds which have a requisite biological activity. Preferably, in order to facilitate synthesis and identification, the compounds in the library are typically formed on solid supports wherein the compound is covalently attached to the support via a cleavable or non-cleavable linking arm. In this regard, libraries of diverse compounds are prepared and then screened to identify "lead compounds" having good binding affinity to the receptor.

Pharmaceutical drug discovery relies heavily on studies of structure-activity relationships wherein the structure of "lead compounds" is typically altered to determine the effect of the alteration on activity. Alteration of the structure of the lead compounds permits evaluation of the effect of the structural alteration on activity. Thus libraries of compounds derived from a lead compound can be created by including derivatives of the lead compound and repeating the screening procedures. In this manner, compounds with the best biological profile, i.e. those that are most active and which have the most ideal pharmacologic and pharmacokinetic properties, can be identified from the initial lead compound.

Thus, the generation of chemical libraries on and off solid resins have proven to be a valuable resource for the pharmaceutical industry in their endeavors to discover new drugs using high throughput screening techniques. In creating the libraries, the compounds are ideally synthesized in situ in solution phase or on a solid support. However, relatively simple synthetic methods to produce a diverse collection of such derivatives in situ are often not available.

Two particular classes of compounds which would be useful for inclusion in screening libraries are hexahydroisoindole and octahydroisoquinoline derivatives. These classes of compounds are known to possess diverse pharmacological and chemical properties and certain members of these classes of compounds are well known to possess biological activity. The following references, hereby incorporated by reference, report the biological activity of such chemical compounds:

Dondio, Giulio; Clarke, Geoffrey D.; Giardina, Giuseppe; Petrillo, Paola; Petrone, Giuseppe; Ronzoni, Silvano; Visentin, Luciano; Vecchietti, Vittorio. The role of the "spacer" in the octahydroisoquinoline series: Discovery of SB 213698, a non-peptidic, potent and selective delta opioid agonist. Analgesia (Elmsford, N. Y.) (1995), 1(4–6), 394–9. CODEN: AALGEB; ISSN: 1071-569X. CAN 124:134781

Clarke, Dondio G.; Giardina, G. D.; Petrillo, P.; Rapalli, L.; Ronzoni, S.; Vecchietti, V. Potent and selective non-peptidic delta opioid ligands based on the novel heterocycle-condensed octahydroisoquinoline structure. Regul. Pept. (1 994), (Suppl. 1), S43–S44. CODEN: REPPDY; ISSN: 0167-0115. CAN 120:260570

Judd, Duncan B.; Brown, Dearg S.; Lloyd, Jane E.; McElroy, Andrew B.; Scopes, David I. C.; Birch, Phillip J.; Hayes, Ann G.; Sheehan, Michael J. Synthesis, antinociceptive activity and opioid receptor profiles of substituted trans-3-(decahydro- and octahydro-4a-isoquinolinyl)phenols. J. Med. Chem. (1992), 35(1), 48–56. CODEN: JMCMAR; ISSN: 0022-2623. CAN 116:41268

Yamaguchi, Toshiaki; Yanagi, Takashi; Hokari, Hiroshi; Mukaiyama, Yuko; Kamijo, Tetsuhide; Yamamoto, Iwao. Preparation and optically active succinic acid derivatives. II. Efficient and practical synthesis of KAD-1229. Chem. Pharm. Bull. (1998), 46(2), 337–340. CODEN: CPBTAL; ISSN: 0009-2363. CAN 128:217248

Commercon, Alain; Lebrun, Alain; Mailliet, Patrick; Peyronel, Jean Francois; Sounigo, Fabienne; Truchon, Alain; Zucco, Martine; Cheve, Michel. New benzisoindole derivatives as inhibitors of farnesyl transferase, their preparation, and pharmaceutical compositions containing them. Fr. Demande, 96 pp. CODEN: FRXXBL. FR2736641 A1 19970117. CAN 127:95194

Hecker, Scott J.; Jefson, Martin R.; McFarland, James W. Preparation of derivatives of rosaramicin, repromicin, 5-mycaminosyltylonide, desmycosin, lactenocin, O-demethyllactenocin, cirramycin A1, and 23-deoxymycaminosyltylonide as antibacterials and antimycoplasmics. U.S., 22 pp. Cont.-in-part of U.S. Ser. No. 996,243, abandoned. CODEN: USXXAM. U.S. Pat. No. 5,545,624A 19960813. CAN 125:248316

Steiner, Gerd; Munschauer, Rainer; Unger, Liliane; Teschendorf, Hans-Juergen; Hoeger, Thomas. Preparation of N-substituted bridged 4,7,8,9-tetrahydroisoindoline derivatives as drugs. Ger. Offen., 6 pp. CODEN: GWXXBX. DE4341400 A1 19950608. CAN 123:285768

Kamijo, Tetsukyo; Yanagi, Takashi; Hokari, Hiroshi; Oda, Juko. Preparation of hexahydroisoindoline derivative as antidiabetic agent. Jpn. Kokai Tokkyo Koho, 6 pp. CODEN: JKXXAF. JP 06340622 A2 19941213 Heisei. CAN 122:213925

Kamijo, Tetsukyo; Yanagi, Takashi; Hokari, Hiroshi; Oda, Juko. Preparation of hexahydroisoindoline derivative as antidiabetic agent. Jpn. Kokai Tokkyo Koho, 6 pp. CODEN: JKXXAF. JP 06340623 A2 19941213 Heisei. CAN 122:187390

Ohnota, Hideki; Kobayashi, Miho; Koizumi, Takashi; Katsuno, Kenji; Sato, Fumiyasu; Aizawa, Toru. In vitro insulinotropic action of a new non-sulfonylurea hypoglycemic agent, calcium (2S)-2-benzyl-3-(cis-hexahydro-2-isoindolinylcarbonyl)propionate dihydrate (KAD-1229), in rat pancreatic B-cells. Biochem. Pharmacol. (1995), 49(2), 165–71. CODEN: BCPCA6; ISSN: 0006-2952. CAN 122:96220

Accordingly, in order to develop new pharmaceutical drugs to treat various disease conditions, it would be highly desirable to be able to generate libraries of diverse hexahydroisoindole and octahydroisoquinoline derivatives optionally attached to a solid support. There is thus a need for a facile in situ method for the generation of a multiplicity of reduced isoindole and isoquinoline compounds.

SUMMARY OF THE INVENTION

This invention is directed to general synthetic methods for preparing hexahydroisoindole, hexahydroisooxyindole and octahydroisooxyquinoline compounds on or off a solid support by employing a mild Diels Alder reaction for the in situ generation of the final compounds. The invention is further directed to the use of these methods to incorporate such reduced isoindole and isooxyquinoline groups in synthetic compound libraries and to libraries containing such compounds.

Hexahydroisoindole, hexahydroisooxyindole, and octahydroisooxyquinoline derivative libraries provided by this invention are synthesized by the Diels Alder cycloaddition reaction of amino acid derived novel triene precursors in accordance with the following general schemes:

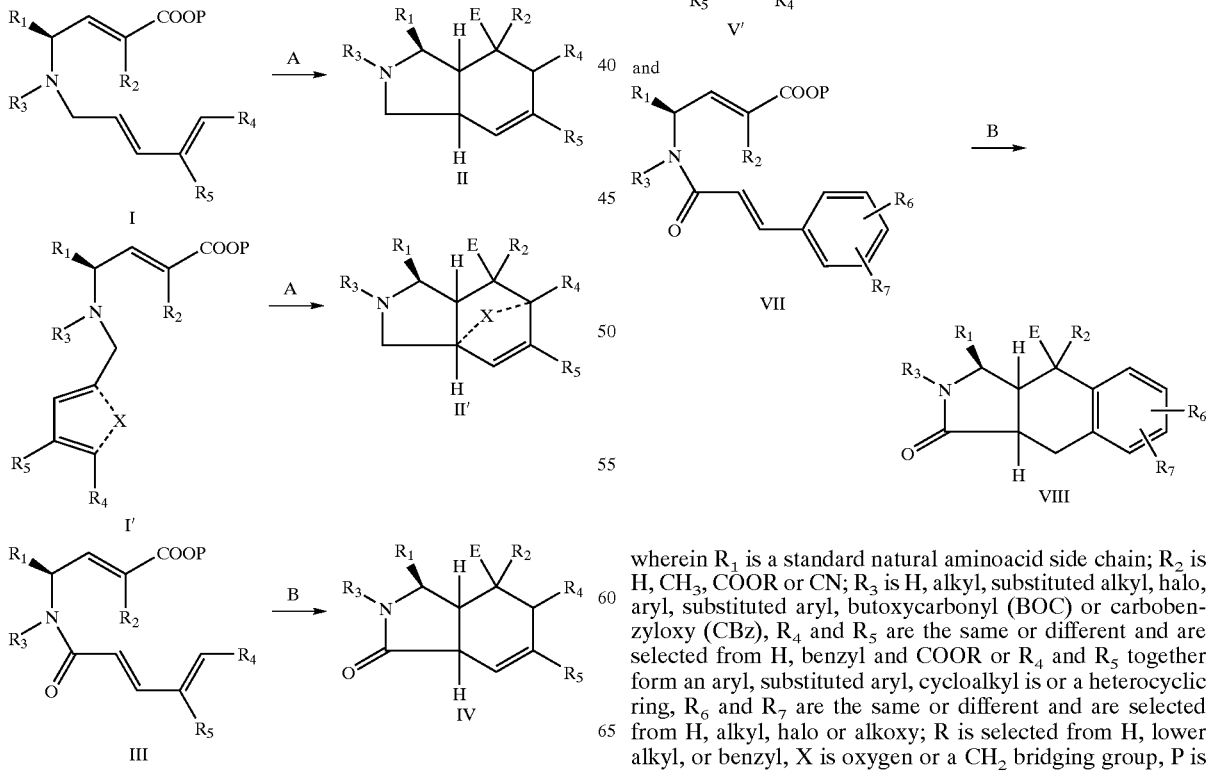

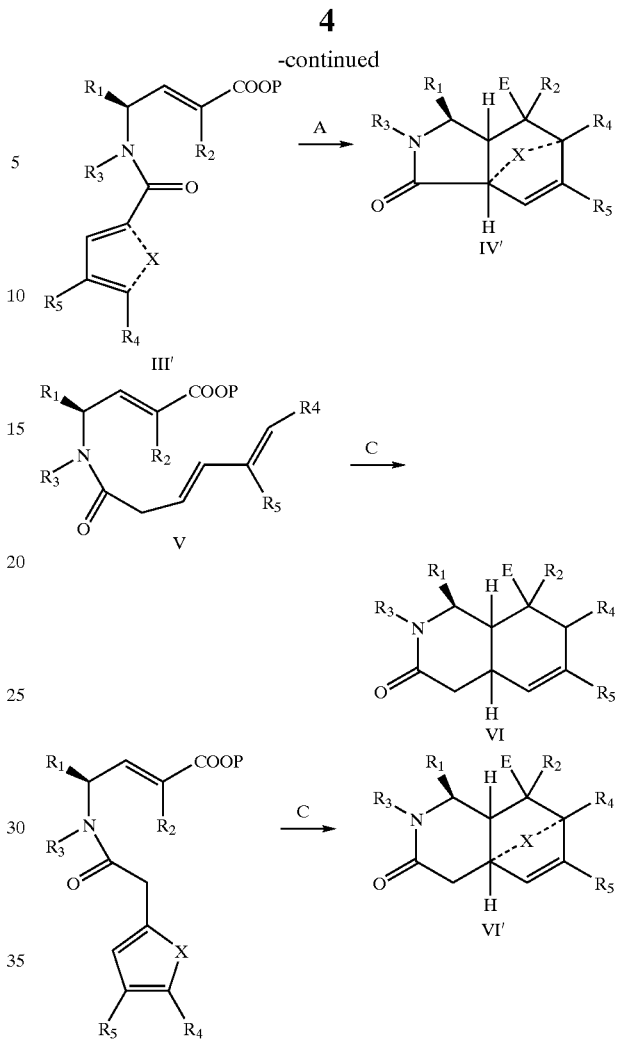

wherein $R_1$ is a standard natural aminoacid side chain; $R_2$ is H, $CH_3$, COOR or CN; $R_3$ is H, alkyl, substituted alkyl, halo, aryl, substituted aryl, butoxycarbonyl (BOC) or carbobenzyloxy (CBz), $R_4$ and $R_5$ are the same or different and are selected from H, benzyl and COOR or $R_4$ and $R_5$ together form an aryl, substituted aryl, cycloalkyl is or a heterocyclic ring, $R_6$ and $R_7$ are the same or different and are selected from H, alkyl, halo or alkoxy; R is selected from H, lower alkyl, or benzyl, X is oxygen or a $CH_2$ bridging group, P is a $C_1$–$C_4$ alkyl group or a solid support resin such as Wang resin, and E is COOP. The carbonyl group of the hexahydroisooxyindole and octahydrooxyquinoline carbonyl compound can optionally be reduced or not introduced to provide the hexahydroisoindole and octahydroisoquinoline derivatives.

The amino acid derived novel triene precursors of Formulas I, I', III, III', V, V', and VII above are another aspect of the invention.

The standard amino acid side chain for $R_1$ may be selected from any of the known natural amino acid groups such as alanine, arginine, asparagine, aspartic acid, cysteine, glutamine, isoleucine, glycine, leucine, histidine, methionine, lysine, phenylalanine, proline, serine, valine, threonine, tryptophane, tyrosine, and the like.

In one embodiment of this invention, the amino acid derived novel triene precursors are covalently attached to a solid support. Solid supports containing such amino acid derived novel triene precursors derivatives may comprise a linking arm which links the solid support to the triene precursor. The linking arm can be either cleavable or non-cleavable. The novel triene precursors attached to the solid support can be used to prepare a library of either solid phase or soluble hexahydroisoindole, hexahydroisooxyindole or octahydroisooxyquinoline derivatives.

The methods described above can be used to create a library of diverse isoindole and isoquinoline derivatives. Accordingly, in one of its composition aspects, this invention is directed to a library of diverse isoindole and isoquinoline derivatives comprising a plurality of solid supports having a plurality of covalently bound isoindole and isoquinoline derivatives, wherein the isoindole and isoquinoline derivative bound to each of said supports is substantially homogeneous and further wherein the isoindole and isoquinoline derivative bound on one support is different from the isoindole and isoquinoline derivatives bound on the other supports. The library is screened to isolate individual compounds that bind to a receptor or possess some desired property.

Accordingly, in one of the embodiments, the invention is directed to a method for synthesizing a plurality of hexahydroisoindole, hexahydroisooxyindole or octahydroisooxyquinoline compounds covalently attached to a solid support which comprises:

a) selecting a solid support comprising at least one compound attached thereto which compound comprises a triene moiety selected from those of the formula:

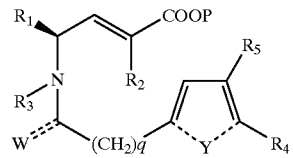

wherein W is Oxygen or hydrogen, q is an integer from zero to one, Y is an oxygen or $CH_2$ bridging group or is H at each carbon atom and $R_1$ to $R_5$ and P are as recited above, and, b) converting said triene moiety to the corresponding hexahydroisoindole, hexahydroisooxyindole or octahydroisooxyquinoline moiety by a Diels Alder cycloaddition reaction.

DETAILED DESCRIPTION

Preferred compounds within the scope of those listed above for formulae I–VII include those compounds wherein $R_1$ is a standard natural amino acid side chain; $R_2$ is H, $CH_3$, COOR or CN; $R_3$ is H, benzyl, substituted benzyl, butoxycarbonyl (BOC) or carbobenzyloxy (CBz), $R_4$ and $R_5$ are the same or different and are selected from H, benzyl and COOR or $R_4$ and $R_5$ together form a saturated or unsaturated carbocyclic ring of 5 or 6 ring atoms or a saturated or unsaturated heterocyclic ring having 5 or 6 ring atoms and 1,2 or 3 hetero atoms selected from nitogen, oxygen and sulfur atoms; R is selected from H, lower alkyl, or benzyl, X is absent or is an oxygen or a $CH_2$ bridging group and P is a $C_1$–$C_4$ alkyl group or a solid support resin such as Wang resin.

Most preferred are those compounds wherein $R_1$ is a standard natural aminoacid side chain; $R_2$ is H, $CH_3$, COOR or CN; $R_3$ is H, benzyl, butoxycarbonyl (BOC) or carbobenzyloxy (CBz), $R_4$ and $R_5$ are the same or different and are selected from H, benzyl and COOR or $R_4$ and $R_5$ together form a saturated or unsaturated carbocyclic ring of 5 or 6 ring atoms or a furan ring; R is selected from H, lower alkyl, or benzyl, X is absent and P is a $C_1$–$C_4$ alkyl group or a solid support resin such as Wang resin.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamine, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$) substituted carbamyl (e.g.CONH alkyl, CONE aryl, CONH aralkyl or cases where there are two substituents on the nitrogen selected from alkyl, aryl or aralkyl), alkoxycarbonyl, aryl, substituted aryl, guanidino and heterocyclos, such as indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "halogen" or "halo" refers to fluroine, chlorine, bromine and iodine.

The term "aryl" refers to monocyclic or bicyclic aromatic hydrocarbon groups having 6 to 12 carbon atoms in the ring portion, such as phenyl, napthyl, biphenyl and diphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocylooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclthio, ureido nitro, cyano, carboxy, carboxyalkyl, carbamyl, alkoxycarbonyl, alkylthiono, arylthiono, alkysulfonyl, sulfonamido, aryloxy and the like. The substitutent may be further substituted by halo, hydroxy, alkyll, alkoxy, aryl, substituted aryl, substituted alkyl or aralkyl. "Substituted bemzyl" refers to a benzyl group substituted by, for example, any of the groups listed above for substituted aryl.

The term "cycloalkyl" refers to optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, oe one or more groups described above as alkyl substitutents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic hetrerocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thizaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropryanyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo[2,3-c]pyridinyl, furo[3,1-b]pyridinyl), or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents.

The term "heteroatoms" shall include oxygen, sulfur and nitrogen.

Throughout this specification, certain abbreviations are employed having the following meanings, unless specifically indicated otherwise. DMF is N,N-dimethyl, formamide, MeOH is methanol, THF is tetrahydrofuran, DIEA is diisopropylethylamine, HATU is O-(7-azabenzotriazol-1-yl)-1,1,3,3-tetramethyluroniumhexafluorosulfate, BOC is butoxycarbonyl, CBZ is carbobenzyloxy, DME is ethylene glycol dimethyl ether.

The generation of chemical libraries on and off resin has proven to be a valuable resource for the pharmaceutical industry in their endeavors to discover new drugs from High Throughput screening. The current invention provides an invention process which allows for the assembly of highly complex drug like molecules with or without defined stereochemistry in 4–5 steps. The key step of this invention is a remarkably facile Intramolecular Diels Alder reaction which allows this complex system to be assembled with regio, stereo and facial selectivity.

In accordance with the invention, novel amino-acid derived triene precursors are prepared, on or off a solid support. These triene precursors undergo a Diels Alder cycloaddition reaction in situ, to yield the complex isoindole, isooxyindole and isooxyquinoline compound libraries of the invention.

Preparation of Hexahydroisooxyindole Compounds

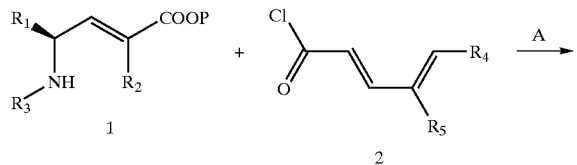

The initial step in the invention involves the acylation of the ester 1 either on or off a solid support with the acid chloride 2. A consists of an appropriate solvent and 1 equivalent of base at from 0–40 C.

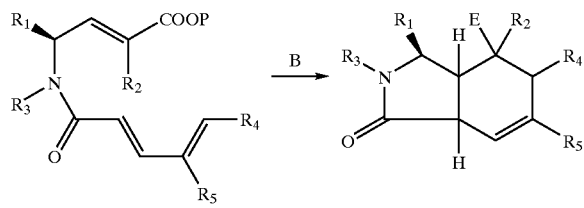

The second step involves the Diels Alder reaction to generate 4. In some cases the reaction of 3 to 4 is so facile that 3 is not isolated. B represents an appropriate solvent such as methylene chloride, an appropriate temperature such as 0–110° C., and the reaction time is 1–64 hours. The reaction temperature and solvent helps determine the product ratios of the cis and trans ring juncture.

Preparation of Hexahydroisoindole Compounds

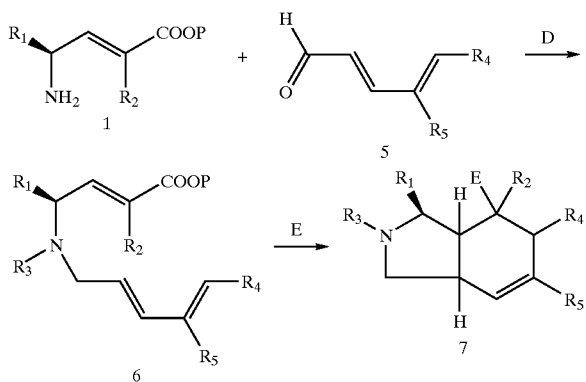

The second part of this invention involves the assembly of the hexahydroisoindole 7. This proceeds through D which represents a reductive amination of 1 with the aldehyde 5 and an appropriate reducing agent such as sodium cyanoborohydride. It then involves the introduction of R3 which in the best cases is a benzoyl or substituted benzoyl group, but can also be other groups such as benzyl, substituted benzyl, BOC, CBz or Tosyl. The introduction of the benzoyl group significantly accelerates the Diels Alder reaction.

Preparation of Octahydroisooxvquinoline Compounds

The third process in this invention involves the thermal Diels Alder where C: is the appropriate solvent such as toluene, xylene, DMF, water or DME; the appropriate temperature such as 80–120° C. and the appropriate reaction time.

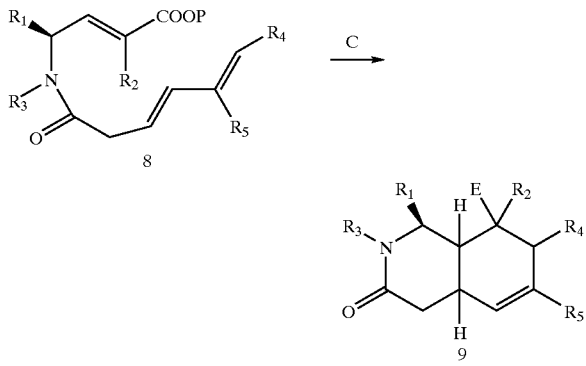

A favored thermal or Lewis acid-catalyzed Diels-Alder reaction normally requires an electron deficient dienophile and an electron-rich diene ([2+4] cycloadditions), or in the case of inverse electron-demand, an electron-rich dienophile and an electron-deficient diene ([4+2] cycloadditions). It is believed that if both the diene and dienophile have the same electron character, i.e., both electron-rich or both electron-deficient, the Diels-Alder reaction is expected only under forcing conditions.

During our studies on Diels-Alder reactions of novel amino acid-derived triene precursors, we found that the cycloaddition proceeds under surprisingly mild thermal conditions between a diene bearing an amide carbonyl group and a dienophile conjugated to an ester carbonyl group. Our observation of mild thermal Diels-Alder cycloadditons that do not have complimentary electron-demand between dienes and dienophiles is unexpected.

The compounds comprising the triene precursor moiety can optionally be covalently attached directly to a solid support or can be attached via a linking arm. The solid support is a material having a rigid or semi-rigid surface which contains or which can be derivatized to contain a reactive functionality which covalently links a compound to the surface thereof. Such materials are well known in the art and include, by way of example, silicon dioxide supports containing reactive Si—OH groups, polyacrylamide supports, polystyrene supports, polyethylene glycol supports and the like. Such supports will preferably take the form of small beads, pellets, disks, or other conventional forms. Linking arms for attaching the triene precursor to the solid support are well known in the art and include, for example, ester, amide, carbamate, ether, thio ether, urea, amine groups and the like.

In those embodiments where a linking arm is employed, the attachment to the solid support is readily cleavable by specific chemical reactions to provide the hexahydroisoindole, hexahydroisooxyindole and octahydroisooxyquinoline compounds free of the solid support. The chemical reactions employed to cleave the attachment to the solid support are selected so as to be specific for the cleavage of the attachment while preventing unintended chemical reactions occurring elsewhere on the compound. For example, where a Wang resin is used as the solid support, trifluoroacetic acid is used to wash the compound from the solid support.

The hexahydroisoindole or octahydroisooxyquinoline compounds which may be prepared by the method of the present invention and which comprise the compounds of the libraries of the invention include those compounds of the formulae II, II', IV, IV', VI, VI' and VIII above.

The following examples are set forth to illustrate the claimed invention and are not to be construed as a limitation thereof.

EXAMPLES

Scheme 1.

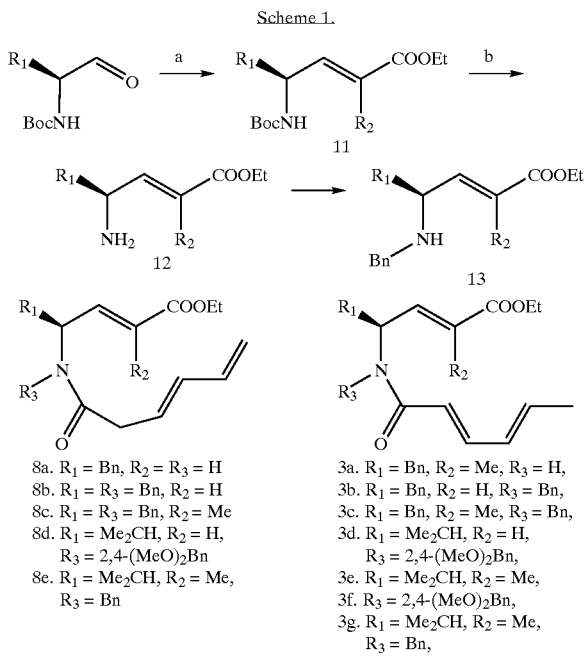

8a. $R_1$ = Bn, $R_2$ = $R_3$ = H
8b. $R_1$ = $R_3$ = Bn, $R_2$ = H
8c. $R_1$ = $R_3$ = Bn, $R_2$ = Me
8d. $R_1$ = Me$_2$CH, $R_2$ = H, $R_3$ = 2,4-(MeO)$_2$Bn
8e. $R_1$ = Me$_2$CH, $R_2$ = Me, $R_3$ = Bn

3a. $R_1$ = Bn, $R_2$ = Me, $R_3$ = H,
3b. $R_1$ = Bn, $R_2$ = H, $R_3$ = Bn,
3c. $R_1$ = Bn, $R_2$ = Me, $R_3$ = Bn,
3d. $R_1$ = Me$_2$CH, $R_2$ = H, $R_3$ = 2,4-(MeO)$_2$Bn,
3e. $R_1$ = Me$_2$CH, $R_2$ = Me,
3f. $R_3$ = 2,4-(MeO)$_2$Bn,
3g. $R_1$ = Me$_2$CH, $R_2$ = Me, $R_3$ = Bn,

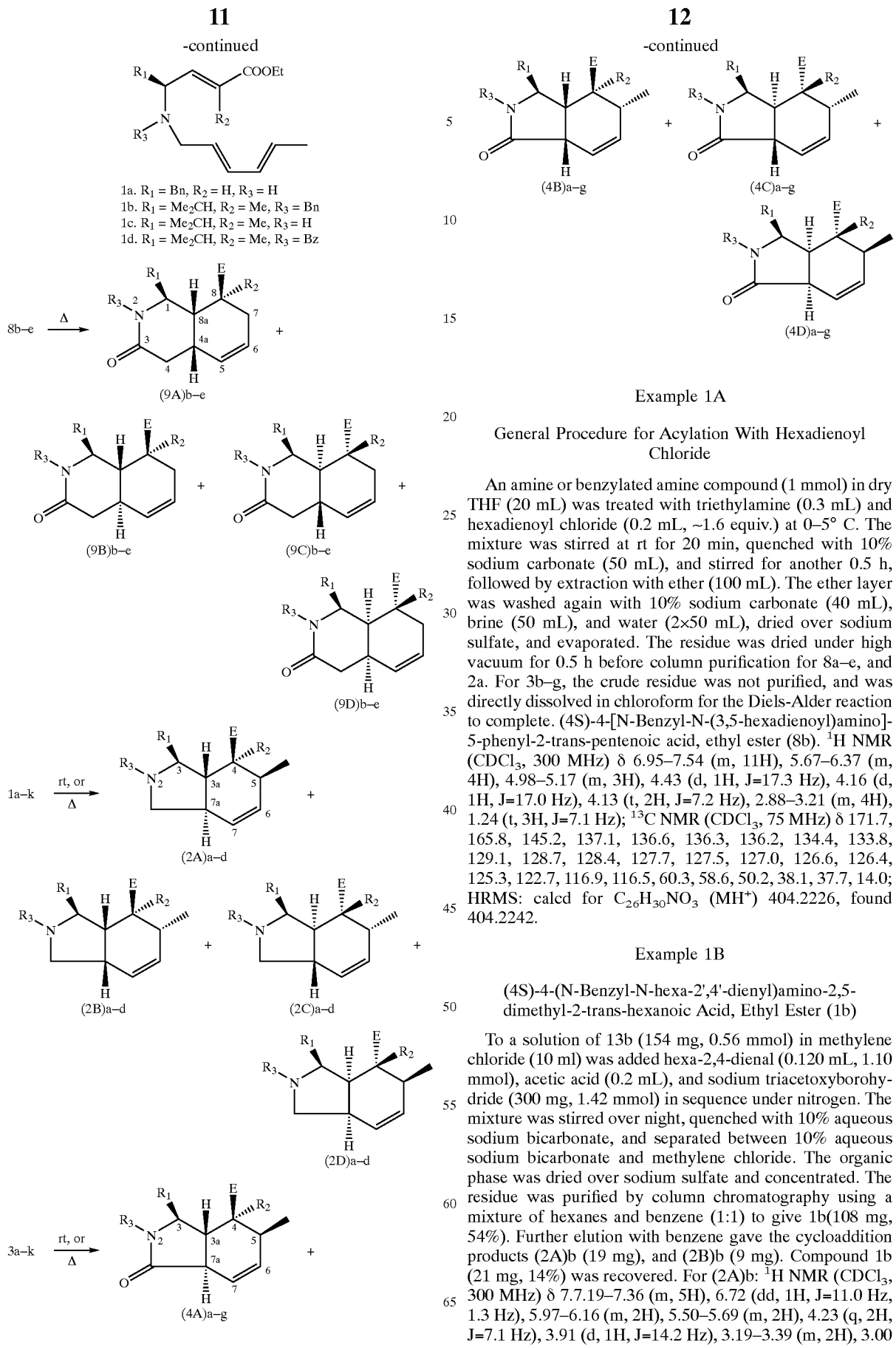

Example 1A

General Procedure for Acylation With Hexadienoyl Chloride

An amine or benzylated amine compound (1 mmol) in dry THF (20 mL) was treated with triethylamine (0.3 mL) and hexadienoyl chloride (0.2 mL, ~1.6 equiv.) at 0–5° C. The mixture was stirred at rt for 20 min, quenched with 10% sodium carbonate (50 mL), and stirred for another 0.5 h, followed by extraction with ether (100 mL). The ether layer was washed again with 10% sodium carbonate (40 mL), brine (50 mL), and water (2×50 mL), dried over sodium sulfate, and evaporated. The residue was dried under high vacuum for 0.5 h before column purification for 8a–e, and 2a. For 3b–g, the crude residue was not purified, and was directly dissolved in chloroform for the Diels-Alder reaction to complete. (4S)-4-[N-Benzyl-N-(3,5-hexadienoyl)amino]-5-phenyl-2-trans-pentenoic acid, ethyl ester (8b). $^1$H NMR (CDCl$_3$, 300 MHz) δ 6.95–7.54 (m, 11H), 5.67–6.37 (m, 4H), 4.98–5.17 (m, 3H), 4.43 (d, 1H, J=17.3 Hz), 4.16 (d, 1H, J=17.0 Hz), 4.13 (t, 2H, J=7.2 Hz), 2.88–3.21 (m, 4H), 1.24 (t, 3H, J=7.1 Hz); $^{13}$C NMR (CDCl$_3$, 75 MHz) δ 171.7, 165.8, 145.2, 137.1, 136.6, 136.3, 136.2, 134.4, 133.8, 129.1, 128.7, 128.4, 127.7, 127.5, 127.0, 126.6, 126.4, 125.3, 122.7, 116.9, 116.5, 60.3, 58.6, 50.2, 38.1, 37.7, 14.0; HRMS: calcd for $C_{26}H_{30}NO_3$ (MH$^+$) 404.2226, found 404.2242.

Example 1B (4S)-4-(N-Benzyl-N-hexa-2',4'-dienyl)amino-2,5-dimethyl-2-trans-hexanoic Acid, Ethyl Ester (1b)

To a solution of 13b (154 mg, 0.56 mmol) in methylene chloride (10 ml) was added hexa-2,4-dienal (0.120 mL, 1.10 mmol), acetic acid (0.2 mL), and sodium triacetoxyborohydride (300 mg, 1.42 mmol) in sequence under nitrogen. The mixture was stirred over night, quenched with 10% aqueous sodium bicarbonate, and separated between 10% aqueous sodium bicarbonate and methylene chloride. The organic phase was dried over sodium sulfate and concentrated. The residue was purified by column chromatography using a mixture of hexanes and benzene (1:1) to give 1b(108 mg, 54%). Further elution with benzene gave the cycloaddition products (2A)b (19 mg), and (2B)b (9 mg). Compound 1b (21 mg, 14%) was recovered. For (2A)b: $^1$H NMR (CDCl$_3$, 300 MHz) δ 7.7.19–7.36 (m, 5H), 6.72 (dd, 1H, J=11.0 Hz, 1.3 Hz), 5.97–6.16 (m, 2H), 5.50–5.69 (m, 2H), 4.23 (q, 2H, J=7.1 Hz), 3.91 (d, 1H, J=14.2 Hz), 3.19–3.39 (m, 2H), 3.00

(t, 1H, J=10.4 Hz), 2.83 (dd, 1H, J=14.4 Hz, 8.5 Hz), 1.80–1.88 (m, 1H), 1.74 (d, 3H, J=4.4 Hz), 1.73 (d, 3H, J=1.1 Hz), 1.34 (t, 3H, J=7.3 Hz), 1.08 (d, 3H, J=6.5 Hz), 0.73 (d, 3H, J=6.6 Hz); $^{13}$C NMR (CDCl$_3$, 75 MHz) δ 167.9, 140.4, 139.9, 132.2, 131.1, 130.7, 129.7, 128.3, 128.1, 128.0, 126.5, 63.0, 60.5, 53.6, 51.4, 29.7, 20.1, 19.9, 17.9, 14.2, 13.3.

Example 1C

Diels-Alder Reaction to Make Compound (9A)b, (9B)b, (9C)b, and (9D)b

Triene 8b (92 mg, 0.23 mmol) in toluene (10 mL) was heated under nitrogen at reflux for 16 h. Toluene was removed in vacuo. The residue was purified by slow column chromatography without air pressure: 8% ethyl acetate in hexanes to elute the fast isomer (14 mg, (9A)b, pure); 10% ethyl acetate in hexanes to elute a second fraction (5 mg, 8b, not pure, containing other isomers); 15–20% ethyl acetate in hexanes to elute a third fraction (66 mg as a mixture of (9A)b and (9c)b with no separation, $^1$H NMR showed a ratio of 3:1). Overall estimated ratio is (9A)b:(9B)b:(9C)b: (9D)b= 33:10:11:3, and the total yield is 94%. The fraction for the mixture of (9A)b and (9C)b was purified in a second round column chromatography using 12% ethyl acetate in hexanes to elute slowly without air pressure. The very initial fractions that were positive in an iodine chamber were identified as (9A)b (6 mg). The last half portion of the eluent was combined to give 16 mg ((9A)b: (9C)b ~1:1), which was purified in a third round of column chromatography similarly to give (9C)b (2 mg) by collecting the very last small fraction.

For (9A)b, $^1$H NMR (CDCl$_3$, 300 MHz) δ 7.11–7.33 (m, 10H), 5.66–5.74 (m, 1H), 5.52–5.61 (m, 1H), 3.29 (d, 1H, J=14.6 Hz), 3.79–3.90 (m, 2H), 3.59–3.70 (m, 2H), 3.02 (dd, 1H, J=4.9 Hz, 13.9 Hz), 2.63–2.83 (m, 3H), 2.44 (dt, 1H, J=6.1 Hz, 10.3 Hz, 10.3 Hz, for H8), 2.26 (dd, 1H, J=9.1 Hz, 18.0 Hz), 2.09–2.17 (m, 2H), 1.96–2.08 (m, 1H); $^{13}$C NMR (CDCl$_3$, 75 MHz) δ 174.1, 168.6, 137.6, 137.3, 129.6, 129.1, 128.9, 128.7, 128.6, 127.5, 126.8, 124.6, 60.4, 58.9, 48.6, 40.0, 38.6, 35.6, 34.9, 28.6, 27.8, 13.9; Observed NOE (CD$_3$OD, 270 K, 400 MHz): medium between H4a and H8a (may be between H7 and H8a due to overlapping of H4a and H7), no NOE between H1 and H8a, H4a and H8, H1 and H4a, H8 and H8a; HRMS: calcd for C$_{26}$H$_{30}$NO$_3$ (MH$^+$) 404.2226, found 404.2242.

For (9B)b, $^1$H NMR (CDCl$_3$, 300 MHz) δ 7.08–7.34 (m, 1OH), 5.65 (d, 1H, J=14.7 Hz), 5.59–6.64 (m, 1H), 5.39 (d, broad, 1H, J=9.6 Hz), 4.05–4.19 (m, 2H), 3.75 (d, 1H, J=14.8 Hz), 3.62 (dt, 1H, J=6.9 Hz, 3.6 Hz, 3.6 Hz, H1), 3.18 (dd, 1H, J=3.8 Hz, 14.1 Hz), 2.34–2.45 (m, 3H), 2.20–2.31 (m, 2H), 2.02–2.11 (m, 1H), 1.81 (dt, 1H, J=6.9 Hz, 10.8 Hz, 10.8 Hz, for H8a), 1.21 (t, 3H, J=7.2 Hz), 1.06 (dd, 1H, J=13.7 Hz, 15.9 Hz for H7'); $^{13}$C NMR (CDCl$_3$, 100 MHz) δ 175.3, 173.2, 137.5, 136.2, 131.0, 129.3, 129.1, 129.9, 128.5, 127.9, 127.4, 126.2, 61.2, 57.4, 47.0, 45.8, 41.7, 38.6, 37.9, 35.4, 30.3, 14.6; Observed NOE (CDCl$_3$, 400 MHz): medium between H1 and H4a, H4 and H8a, weak between H1 and H8a, H8 and H8a, no between H4a and H8a; HRMS: calcd for C$_{26}$H$_{30}$NO$_3$ (MH$^+$) 404.2226, found 404.2221.

For (9C)b, $^1$H NMR (CDCl$_3$, 300 MHz) δ 6.92–7.33 (m, 10H), 5.62–5.74 (m, 1H), 5.46–5.54 (m, 1H), 5.34 (d, 1H, J=15.1 Hz), 3.84–3.93 (m, 2H), 3.72 (dt, 1H, J=4.3 Hz, 4.3 Hz, 8.6 Hz, H1), 3.10 (dd, 1H, J=3.7 Hz, 13.9 Hz), 3.00 (d, 1H, J=15.1 Hz), 2.56–2.72 (m, 3H), 2.12–2.38 (m, 3H), 1.97 (dt, 1H, J=4.1 Hz, 11.5 Hz, 11.5 Hz, H8a), 1.01 (t, 3H, J=7.1 Hz); $^{13}$C NMR (CDCl$_3$, 100 MHz) δ 173.9, 169.7, 138.9, 137.4, 129.6, 129.1, 128.8, 128.3, 128.0, 127.8, 127.5, 127.1, 124.8, 60.9, 58.7, 49.2, 42.7, 42.5, 38.0, 37.5, 30.3, 29.6, 14.2; Observed NOE (CDCl$_3$, 400 MHz): strong between H1 and H8a, medium between H4a and H9, no NOE between H4a and H8a; $^1$H decoupling NMR (CDCl$_3$, 400 MHz) at 1.97 gave J$_{8a-1}$=4.3 Hz; HRMS: calcd for C$_{26}$H$_{30}$NO$_3$ (MH$^+$) 404.2226, found 404.2239.

Example 1D

Diels-Alder Reaction to Make Compounds (9A)c and (9B)c

Triene 8c (116 mg, 0.28 mmol) in toluene (10 mL) was heated under nitrogen at reflux for 50 h. Toluene was removed in vacuo. The residue was purified by slow column chromatography without air pressure: a mixture of benzene and hexanes (1:1) was used to pack column and load the sample; 5% and then 10% ethyl acetate in hexanes to elute the unreacted starting material (9 mg, 8%); 15% ethyl acetate in hexanes to elute the fast isomer (9B)c (24 mg, 21%, oil); 20% and 30% ethyl acetate in hexanes to elute a second fraction (9A)c (74 mg, 64%, oil).

For (9A)c, $^1$H NMR (CDCl$_3$, 300 MHz) δ 7.18–7.38 (m, 10 H), 5.50 (d, 1H, J=14.4 Hz), 5.37–5.42 (m, 1H), 5.30 (d, broad, 1H, J 10.3 Hz), 4.02 (q, 2H, J 7.1 Hz), 3.46 (d, 1H, J=14.4 Hz), 3.27–3.32 (m, 1H, H1), 3.03 (dd, 1H, J=6.5 Hz, 13.4 Hz), 2.79 (dd, 1H, J=5.0 Hz,13.4 Hz), 2.63 (s, broad, 2H, H4a and H8a), 2.24 (dd, 1H, J=2.8 Hz, 15.5 Hz), 2.04 (dd, 1H, J=4.4 Hz, 18.1 Hz), 1.91 (dd, 1H, J=4.3 Hz, 15.5 Hz), 1.16 (t, 3H, J=7.0 Hz), 0.76 (s, 3H), 0.63 (dd, 1H, J=2.4 Hz, 17.9 Hz); $^{13}$C NMR (CDCl$_3$, 75 MHz) δ 176.2, 170.3, 136.7, 136.6, 130.1, 129.6, 128.6, 128.5, 128.1, 127.6, 127.2, 127.0, 60.5, 54.9, 47.4, 45.1, 42.6, 40.5, 36.4, 31.3, 29.4, 23.2, 13.8; Observed NOE (CD$_3$OD, 400 MHz): between H4a and H8a, H1 and Me8, H1and H7; HRMS: calcd for C$_{27}$H$_{32}$NO$_3$ (MH$^+$) 418.2382, found 418.2388.

For (9B)c, $^1$H NMR (CDCl$_3$, 300 MHz) δ 7.08–7.36 (m, 10 H), 5.64 (d, 1H, J=14.7 Hz), 5.55–5.60 (m, 1H), 5.36 (d, broad, 1H, J=10.7 Hz), 4.08–4.27 (m, 2H), 3.58 (d, 1H, J=14.5 Hz), 3.49–3.54 (m, 1H, H1), 3.07 (dd, 1H, J=3.7 Hz, 14.0 Hz), 2.86 (d, broad, 1H, J=19.6 Hz), 2.30 (dd, 1H, J=4.4 Hz, 14.0 Hz), 2.20 (dd, 1H, J=1.9 Hz, 15.6 Hz), 1.85–2.01 (m, 3H), 1.29 (t, 3H. J=7.2 Hz), 0.98 (dd, 1H, J=12.7 Hz, 15.4 Hz), 0.69 (s, 3H); $^{13}$C NMR (CDCl$_3$, 100 MHz) δ 177.0, 173.5, 137.6, 136.5, 131.0, 129.0, 129.0, 128.9, 128.3, 128.0, 127.5, 125.8, 61.4, 55.0, 47.2, 45.2, 44.5, 38.8, 38.2, 37.4, 31.7, 16.2, 14.5; Observed NOE (CD$_3$OD, 400 MHz): medium between H1 and Me8, and between H4a and Me8; HRMS: calcd for C$_{27}$H$_{32}$NO$_3$ (MH$^+$) 418.2382, found 418.2382.

Example 1E

Diels-Alder Reaction to Make Compounds (4A)a and (4B)a

Triene 3a (96 mg, 0.29 mmol) in toluene (10 mL) was heated under nitrogen at reflux for 7 h. Toluene was removed in vacuo. The residue was purified by slow column chromatography without air pressure: the fast isomer was eluted with 0.5% methanol in methylene chloride to give (4A)a (65 mg, 68%); The slow isomer was eluted with 1% methanol in methylene chloride to give (4B)a (21 mg, 22%).

For (4A)a, $^1$H NMR (CDCl$_3$, 300 MHz) δ 7.14–7.35 (m, 5H), 6.09 (dt, 1H, J=2.1 Hz, 2.1 Hz, 9.7 Hz), 5.60 (dt, 1H, J=3.4 Hz, 3.4 Hz, 9.7 Hz), 5.23 (s, broad, 1H), 4.11–4.28 (m, 2H), 3.74 (ddd, 1H, J=3.4 Hz, 9.8 Hz, 12.3 Hz, H3), 3.12 (dd, 1H, J=3.2 Hz, 13.9 Hz), 2.82 (dd, 1H, J=2.5 Hz, 13.2 Hz, H7a), 2.51 (dd, 1H, J=12.5 Hz, 13.2 Hz), 2.45 (dd, 1H, J=9.3 Hz, 13.2 Hz, H3a), 2.18–2.22 (m, 1H), 1.37 (s, 3H), 1.32 (t, 3H, J=7.1 Hz), 1.01 (d, 3H, J=7.3 Hz); $^{13}$C NMR (CDCl$_3$, 75 MHz) δ 175.0, 173.9, 137.9, 133.0, 128.9, 128.6, 126.9, 121.8, 60.6, 56.0, 48.9, 46.3, 43.2, 41.7, 40.5, 18.2, 17.9, 14.0; $^1$H NMR coupling constants: 13.2 Hz between H3a and H7a, 9.3–9.8 Hz between H3 and H3a; HRMS: calcd for $C_{20}H_{26}NO_3$ (MH$^+$) 328.1913, found 328.1915.

For (4B)a, $^1$H NMR (CDCl$_3$, 300 MHz) δ 7.13–7.34 (m, 5H), 5.93 (dt, 1H, J=3.3 Hz, 3.3 Hz, 9.9 Hz), 5.69 (d, 1H, NH), 5.50 (dt, 1H, J=2.1 Hz, 2.1 Hz, 9.9 Hz), 4.01–4.09 (m, 1H), 3.83–3.95 (m, 1H), 3.52 (t, broad, 1H, J=6.8 Hz, H3), 3.04 (dd, 1H, J=3.2 Hz, 8.9 Hz, H7a), 2.88 (d, 1H, J=8.9 Hz, H3a), 2.72–2.82 (m, 2H), 2.63–2.72 (m, 1H), 1.22 (t, 3H, J=7.2 Hz), 0.93 (s, 3H), 0.91 (t, 3H, J=7.3 Hz); $^{13}$C NMR (CDCl$_3$, 75 MHz) δ 176.03, 175.97, 136.9, 132.3, 129.2, 128.6, 126.7, 121.5, 60.7, 55.5, 48.1, 44.9, 42.2, 39.2, 35.8, 15.9, 14.2, 10.1; Observed NOE (CDCl$_3$, 400 MHz): between H3a and H7a, H3 and Me4, H3a and H5; HRMS: calcd for $C_{20}H_{25}NO_3$ (M$^+$) 327.1834, found 327.1829.

Example 1F

Diels-Alder Reaction to Make Compounds (4A)b and (4C)b

The crude triene 3b, prepared from 13 (90 mg, 0.29 mmol) by following the General Procedure for Acylation, was dissolved in chloroform and kept in the dark. The Diels-Alder reaction was monitored by $^1$H NMR (A small part of the solution was taken in a separate flask; chloroform was blown away with nitrogen; the residue was dissolved in CDCl$_3$). The cycloaddition was complete in 12 h. $^1$H NMR showed a isomeric product ratio of 10:10:1:1. The residue was purified by slow column chromatography without air pressure: a mixture of benzene and hexanes (1:1) was used to pack column and load the sample; 5% ethyl acetate in hexanes to elute the fast isomer (4A)b (46 mg, 39%); 8% ethyl acetate in hexanes to elute a second pure isomer (4C)b (6 mg) and a third fraction of (4C)b (44 mg) containing minor (4A)b and (4D)b.

For (4A)b, $^1$H NMR (CDCl$_3$, 300 MHz) δ 6.50–7.36 (m, 10H), 6.15 (d, 1H, J=9.6 Hz), 5.55 (dt, 1H, J=3.3 Hz, 9.7 Hz), 5.11 (d, 1H, J=15.3 Hz), 3.96–4.16 (m, 3H), 3.68 (ddd, 1H, J=3.1 Hz, 5.8 Hz, 9.0 Hz, H3), 3.39 (dd, 1H, J=3.0 Hz, 15.6 Hz), 3.01 (dd, 1H, J=5.7 Hz, 15.7 Hz), 2.93 (dd, 1H, J=6.6 Hz, 11.0 Hz, H4), 2.70–2.87 (m, 2H), 2.12 (dt, 1H, 9.9 Hz, 11.2 Hz, 11.2 Hz, H3a), 1.21 (t, 3H, J=7.2 Hz), 0.95 (d, 3H, J=7.2 Hz); $^{13}$C NMR (CDCl$_3$, 75 MHz) δ 173.0, 172.6, 137.7, 136.7, 133.2, 129.5, 128.5, 128.3, 127.7, 127.2, 126.4, 123.0, 60.4, 59.8, 48.7, 47.7, 44.2, 39.6, 36.2, 34.1, 17.4, 14.2; Observed NOE: strong between H3a and Me5, H4 and H5, medium between H3 and H4, H3 and H7a, H3 and H3a, H3a and H4; HRMS: calcd for $C_{26}H_{30}NO_3$ (MH$^+$) 404.2226, found 404.2241.

For (4C)b, $^1$H NMR (CDCl$_3$, 300 MHz) δ 6.90–7.34 (m, 10 H), 6.12 (d, 1H, J=9.8 Hz), 5.58 (dt, 1H, J=3.4 Hz, 3.4 Hz, 9.8 Hz), 4.95 (d, 1H, J=14.9 Hz), 3.91–4.08 (m, 3H), 3.20 (d, 1H, J=14.9 Hz), 3.00 (dd, 1H, J=7.0 Hz, 12.0 Hz, H4), 1.36 (m, 1H, H7a), 2.76 (m, 1H, H5), 2.65–2.78 (m, 2H), 2.78 (dt, 1H, J=6.5 Hz, 12.6 Hz, 12.6 Hz, H3a), 1.19 (t, 3H, J=7.2 Hz), 0.89 (d, 3H, J=7.1 Hz); $^{13}$C NMR (CDCl$_3$, 75 MHz) δ 172.8, 172.5, 138.1, 136.7, 133.0, 129.3, 128.7, 128.5, 128.1, 127.4, 126.7, 122.8, 60.4, 58.7, 45.2, 45.0, 42.6, 39.8, 34.2, 33.2, 17.0, 14.1; Observed NOE: between H4 and H8, H7a and H8, H4 and H7a, H3a and Me5, H4 and H5; HRMS: calcd for $C_{26}H_{30}NO_3$ (MH$^+$) 404.2226, found 404.2238.

Example 1G

Diels-Alder Reaction to Make Compounds (2A)g and (2C)g

Compound 3a (110 mg, 2.11 mmol) after removal of Boc group was used for reductive alkylation with 2,4-hexadienal by following the procedure to make 1b and c. The reduction was allowed for 6 h after addition of triacetoxyborohydride. $^1$H NMR of the crude mixture indicated the completion of the cycloaddition of 2 g, and showed two diastereomers ((2A)a: (2C)a=5:1). The major and more polar isomer (2A)a was isolated in pure form (68 mg, 66%), eluted with 20–30% ethyl acetate in hexanes from column chromatography. $^1$H NMR (CDCl$_3$, 300 MHz) δ 7.16–7.31 (m, 5H), 5.75 (dt, 1H, J=9.8 Hz, 1.7 Hz), 5.56 (dt, 1H, J=9.7 Hz, 3.3 Hz), 4.18 (q, 2H, J=7.1 Hz), 3.20–3.29 (m, 2H), 3.03 (dd, 1H, J=8.5 Hz, 7.0 Hz, H3), 2.90 (dd, 1H, J=11.3 Hz, 6.8 Hz, H7), 2.74–2.85 (m, 1H, H6), 2.59 (dd, 1H, J=12.5 Hz, 10.0 Hz, H8'), 2.53 (dd, 1H, J=11.9 Hz, 8.6 Hz, H3'), 2.36–2.46 (m, 1H, H3a), 1.75 (q, 1H, 11.1 Hz) 1.30 (t, 3H, J=7.1 Hz), 1.02 (d, 3H, J=7.2 Hz); $^{13}$C NMR (CDCl$_3$, 75 MHz) δ 173.4, 140.0, 132.9, 129.0, 128.2, 125.8, 61.3, 60.0, 48.2, 47.6, 45.2, 44.6, 41.5, 33.5, 29.6, 17.8, 14.2; HRMS: calcd for $C_{19}H_{26}NO_2$ (MH$^+$) 300.1965, found 300.1953.

Example 1H

Diels-Alder Reaction to Make Compounds (2A)b and (2B)b

Compound 1b (101 mg), after isolation from column chromatography, was immediately dissolved in deuterated chloroform. The cycloaddition was complete in 15 days as monitored by $^1$H NMR, and gave two isomers in a 3:2 ratio. The mixture was eluted first with a mixture of benzene and hexanes (1:1) to remove impurities, then with benzene to give the minor isomer (2B)b (32 mg), and finally with 5% ethyl acetate in hexanes to give the major isomer (2A)b (52 mg). Total yield was 84%.

For (2A)b, $^1$H NMR (CDCl$_3$, 300 MHz) δ 7.19–7.41 (m, 5H), 5.71 (dt, 1H, J=9.6 Hz, 2.0 Hz), 5.54 (dt, 1H, J=9.6 Hz, 3.0 Hz), 4.02–4.22 (m, 2H), 3.85 (d, 1H, J=13.4 Hz), 3.66 (d, 1H, J=13.4 Hz), 2.61–2.68 (m, 2H), 2.52 (t, 1H, J=11.0 Hz, H1), 2.22–2.32 (m, 1H, H7a), 2.16 (dd, 1H, J=11.5 Hz, 9.7 Hz, H3a), 2.12 (m, 1H, H5), 1.70 (m, 1H, isopropyl), 1.28 (t, 3H, J=7.1 Hz), 1.25 (s, 3H), 0.97–1.02 (5 peaks, 9H); $^{13}$C NMR (CDCl$_3$, 75 MHz) δ 176.2, 141.7, 133.6, 128.1, 128.0, 127.4, 126.5, 69.8, 63.7, 60.2, 55.5, 48.5, 46.8, 42.2, 37.5, 30.7, 22.4, 18.3, 18.1, 15.8, 14.2; HRMS: calcd for $C_{23}H_{34}NO_2$ (MH$^+$) 356.2589, found 356.2578; Observed NOE (CDCl$_3$, 600 MHz): H3-Me4, H7a-Me4, H3-H5, H5-Me4.

For (2B)a, $^1$H NMR (CDCl$_3$, 300 MHz) δ 7.18–7.34 (m, 5H), 5.62 (dt, 1H, J=9.9 Hz, 3.2 Hz), 5.36 (d, broad, 1H, J=9.9 Hz), 3.98–4.24 (m, 3H), 3.55 (d, 1H, J=13.6 Hz), 2.94 (t, 1H, J=7.9 Hz), 2.74–2.90 (m, 3H), 2.37 (dd, 1H, J=8.5 Hz, 2.2 Hz, H3a), 2.16 (dd, 1H, 12.0 Hz, 8.2 Hz), 1.67–1.80 (m, 1H), 1.28 (t, 3H, J=7.1 Hz) 1.00 (s, 3H), 0.94 (d, 3H, J=6.8 Hz), 0.88 (d, 3H, J=7.3 Hz), 0.84 (d, 3H, J=6.9 Hz); $^{13}$C NMR (CDCl$_3$, 75 MHz) δ 177.3, 140.9130.9, 128.2, 128.1, 126.6, 125.7, 60.5, 59.3, 58.3, 48.2, 46.4, 39.5, 37.1, 32.8, 18.5, 17.9, 16.5, 14.1, 13.3; Observed NOE (CDCl$_3$, 400 MHz): H3a-H5, H3a-H7a, H3-Me4.

Example 1I

Diels-Alder Reaction to Make Compound (2A)c

To the primary amine triene Ic (110 mg, 0.415 mmol) in THF (10 mL) were added Et₃N (0.4 ml) and PhCOCl (70 mL, 0.60 mmol). The mixture was stirred for 0.5 h, quenched with 5% NaHCO₃ (50 mL), and extracted with ether. The ether layer was dried over MgSO₄ (0.5 h), evaporated, and pumped under high vacuum for 1 h. A part of the residue was dissolved in CDCl₃, and the second part was dissolved in C₆D₆. The reaction was monitored by $^1$H NMR, and was found complete in 18 h in either CDCl₃, or C₆D₆ (the time was counted immediately after the addition of PhCOCl).The $^1$H NMR showed a mixture of 2 isomers in a ratio of 9:1. Column chromatography using 5–10% ethyl acetate in hexanes gave the pure major isomer (2A)c (89mg, 58%), and a fraction of mixtures (5 mg, 3%). The total yield is 61%. For (2A)c, $^1$H NMR (C₆D₆, 300 MHz) δ 7.64–7.68 (m, 2H), 7.09–7.16 (m, 3H), 5.42–5.52 (m, 2H), 4.63 (d, broad, 1H, J=8.2 Hz, H1), 3.84–3.95 (m, 2H), 3.45 (dd, 1H, J=6.6 Hz, 9.6 Hz), 2.84 (dd, 1H, J=10.3 Hz, 11.6 Hz), 2.56–2.68 (m, 1H), 2.43 (dd, 1H, J=10.0 Hz, 11.8 Hz, H3a), 1.72–1.80 (m, 2H), 1.21 (d, 3H, J=7.0 Hz), 1.17 (s, 3H), 0.90 (m, 9H); $^{13}$C NMR (CDCl₃, 75 MHz) δ 176.0, 171.0, 137.0, 134.8, 133.6, 130.3, 128.4, 128.3, 127.9, 127.6, 61.5, 60.5, 54.4, 49.5, 47.4, 42.0, 40.4, 30.7, 19.8, 18.8, 17.4, 16.7, 14.2; Observed NOE (C₆D₆, 400 MHz): H3-Me4.

Example 2

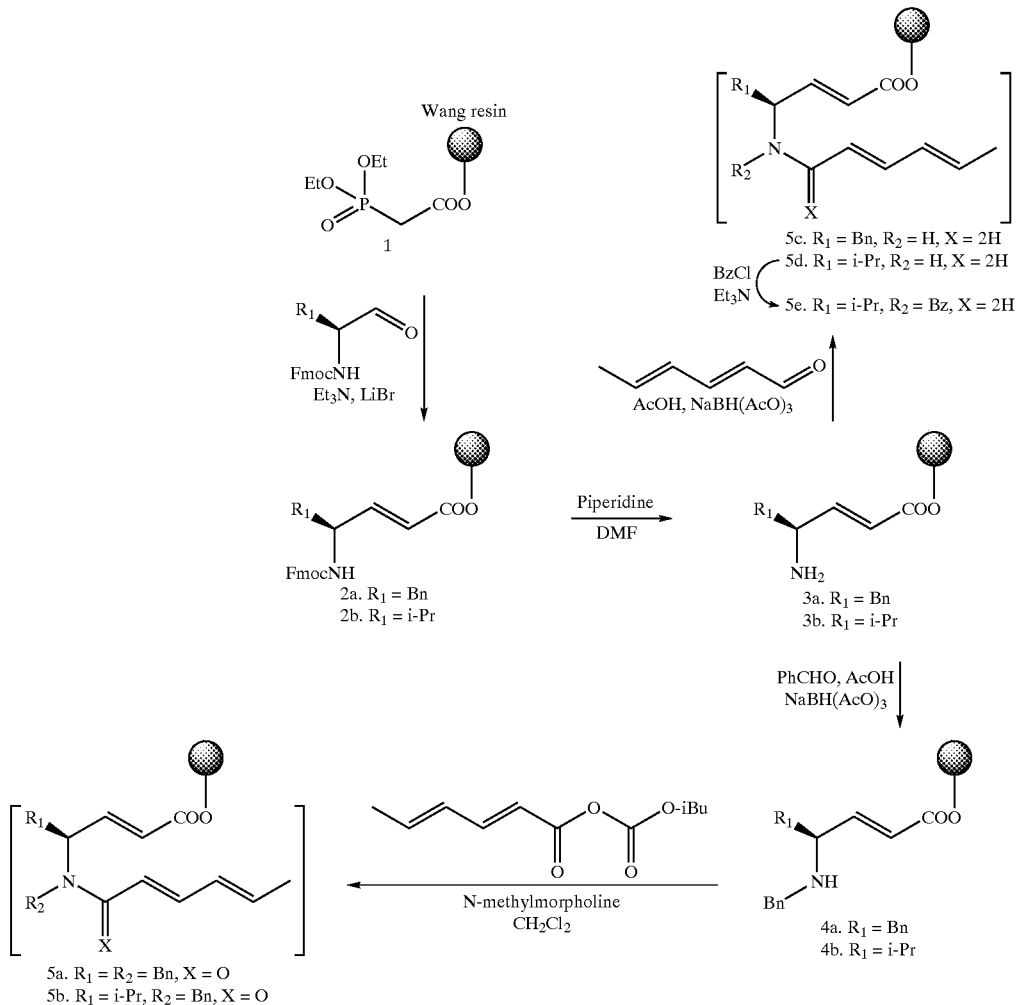

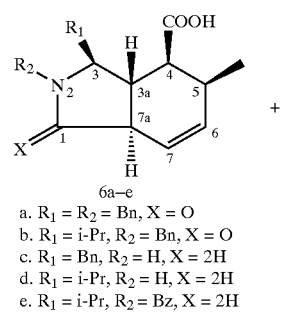

-continued

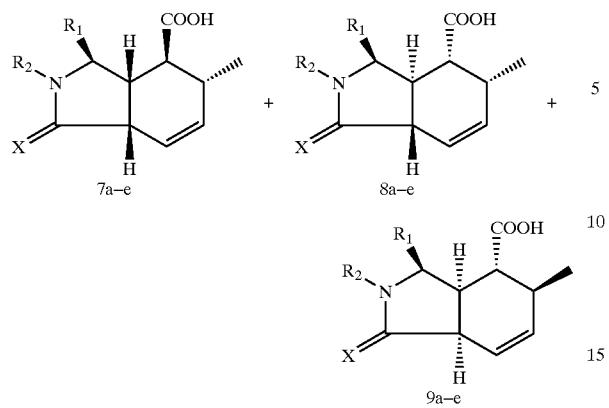

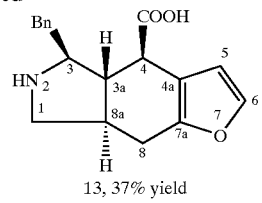

13, 37% yield

Scheme 5

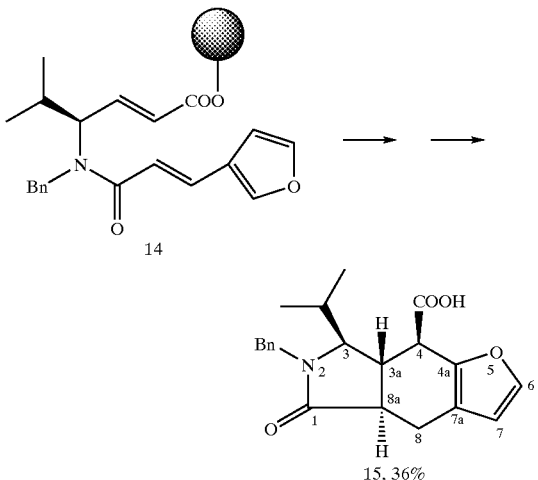

Example 2A

Preparation of 3a–b

Diethyl phosphonoacetyl-Wang resin (1.575 g, 1.103 mmol, 0.70 mmol/g) in THF (15 mL) was treated with $Et_3N$ (1 mL), LiBr (200 mg), and a Fmoc protected amino aldehyde (3 equiv.). The mixture was shaken for 20 h, washed 3 rounds with MeOH, $CH_2Cl_2$ and water, dried in vacuo, and treated with 20% piperidine in DMF for 20 min. Filtration followed by washing gave the resin bound amines 3a–b, which turned blue upon a qualitative ninhydrin test.

Example 2B

Procedure for Reductive Alkylation to Make 4a–b, 5c–d, 10c–d, and 12

An amine 3a or 3b in $CH_2Cl_2$ containing glacial AcOH (10%) was treated with an aldehyde (10 equiv; benzaldehyde for 4a–b, E,E-2,4-hexadienal for 5c–d, fural for 10c, 5-hydroxymethylfural for 10d, or E-3-furanacrolein for 12) for 0.5 h on a shaker. The mixture was washed with $CH_2Cl_2$, DMF, and $CH(OMe)_3$ and was treated with $NaBH(OAc)_3$ (3 equiv) in anhydrous $CH(OMe)_3$ containing 10% glacial AcOH for 1 h. After washing, the resin-bound intermediates were used for the next steps.

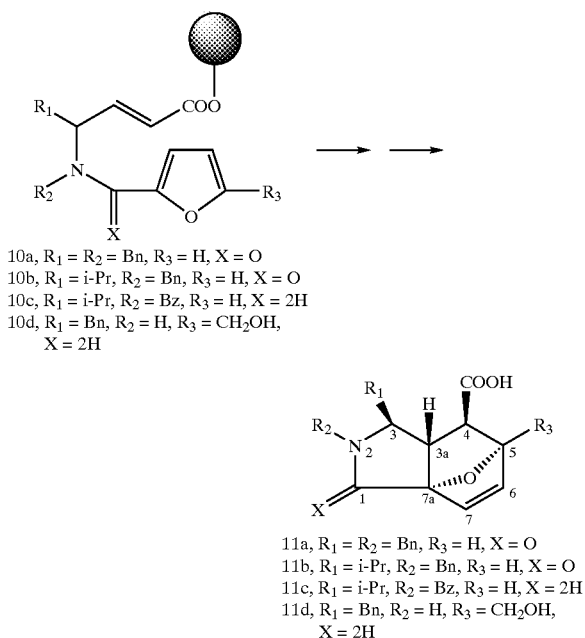

10a, $R_1 = R_2 = Bn, R_3 = H, X = O$
10b, $R_1 = i\text{-}Pr, R_2 = Bn, R_3 = H, X = O$
10c, $R_1 = i\text{-}Pr, R_2 = Bz, R_3 = H, X = 2H$
10d, $R_1 = Bn, R_2 = H, R_3 = CH_2OH, X = 2H$ 11a, $R_1 = R_2 = Bn, R_3 = H, X = O$
11b, $R_1 = i\text{-}Pr, R_2 = Bn, R_3 = H, X = O$
11c, $R_1 = i\text{-}Pr, R_2 = Bz, R_3 = H, X = 2H$
11d, $R_1 = Bn, R_2 = H, R_3 = CH_2OH, X = 2H$ Scheme 4

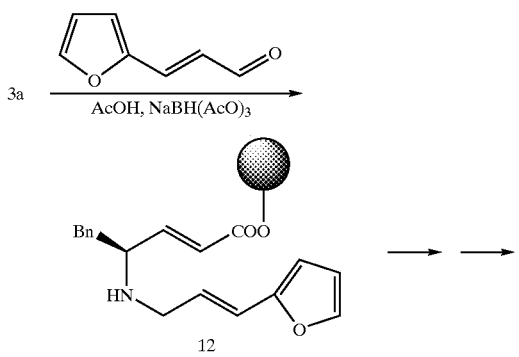

Example 2C

Coupling Acylation and Diels-Alder Reactions to Prepare 6a, and 8a

To 2,4-hexadienoic acid (163 mg, 1.46 mmol) in $CH_2Cl_2$ (10 mL) at 0° C. was added N-methylmorpholine (1.0 mL) and isobutyl chloroformate (200 µL, 1.39 mmol). The mixture was stirred at rt for 15 min, and was added to a tube that contained resin-bound intermedaite 4a (610 mg, 0.403 mmol). The tube was shaken over night. The mixture was then washed with $CH_2Cl_2$ and MeOH, and was allowed to stay in $CH_2Cl_2$ for further 30 h with occasional swirling. After filtration, the resin was treated with 20% TFA in $CH_2Cl_2$ for 20 min. The TFA solution was collected by filtration, and the solid resin residue was washed thoroughly with $CH_2Cl_2$ and $CH_3OH$. The combined filtrate was concentrated in vaccue, co-evaporated with $CHCl_3$, and dried under high vacuum for 0.5 h. MS analysis of the crude mixture showed a clean peak of 376 for the protonated molecular ions ($MH^+$). Reverse phase HPLC analysis on Gilson C-18 column using a mobile phase gradient of MeCN (30–70% in 35 min) in water (containing 0.1% TFA) showed a ratio of about 10:10:3:1. The slowest isomer 6a was obtained as one of the majors in total 30 mg (20%) in 3 rounds of preparative HPLC. The next slowest isomer 8a was obtained in total 27 mg (18%). There were two peaks with smaller retention times as the possible minor isomers, and were not characterized due to the small quantities and some impurities.

For 6a, $^1$H NMR (300 MHz, $CDCl_3$) δ 7.12–7.26 (m, ~8H), 6.89–6.93 (m, 2H), 6.15 (d, 1H, J=9.7 Hz), 5.54 (dt, 1H, J=3.2 Hz, 3.2 Hz, 9.6 Hz), 5.12 (d, 1H, J=15.2 Hz), 4.04 (d, 1H, J=15.2 Hz), 3.63 (ddd, 1H, J=3.1 Hz, 5.6 Hz, 9.0 Hz, H3), 3.36 (dd, 1H, J=3.0 Hz, 15.5 Hz), 2.92–3.03 (m, 2H), 2.71–2.84 (m, 2H), 2.08 (q, 1H, J=5 11.0 Hz, H3a), 0.98 (d, 3H, J=7.1 Hz); $^{13}$C NMR (75 MHz, $CDCl_3$) δ 176.7, 173.1, 137.3, 136.5, 133.0, 129.5, 128.5, 128.4, 127.7, 127.3, 126.5, 123.0, 59.7, 48.3, 47.7, 44.2, 39.5, 36.2, 33.9, 17.2; LC-MS: calcd for $C_{24}H_{26}NO_3$ ($MH^+$) 376, found 376.

For 8a, $^1$H NMR (300 MHz, $CDCl_3$) δ 7.23–7.31 (m, 6H), 7.11–7.15 (m, 2H), 6.88–6.93 (m, 2H), 6.13 (d, 1H, J=9.8 Hz), 5.59 (dt, 1H, J=3.5 Hz, 3.5 Hz, 9.9 Hz), 4.94 (d, 1H, J=15.1 Hz), 3.96–4.03 (m, 1H, H3), 3.19 (d, 1H, J=15.0 Hz), 3.07 (dd, 1H, J=6.8 Hz, 12.0 Hz, H4), 3.00 (dd, 1H, J=0.9 Hz, 12.7 Hz, H7a), 2.68–2.84 (m, 3H), 2.27 (dt, 1H, J=6.6 Hz, 12.4 Hz, 12.4 Hz, H3a), 0.96 (d, 3H, J=7.1 Hz); $^{13}$C NMR (75 MHz, $CDCl_3$) δ 176.4, 173.0, 137.9, 136.6, 132.8, 129.3, 128.8, 128.6, 128.0, 127.5, 126.9, 122.7, 58.8, 45.2, 44.8, 42.7, 39.5, 34.2, 33.1, 16.9; LC-MS: calcd for $C_{24}H_{26}NO_3$ ($MH^+$) 376, found 376.

Example 2D

Coupling Acylation and Diels-Alder Reaction to Prepare 6b

By following the procedure to prepare 6a and 8a, resin 4b1 (500 mg, 0.364 mmol) was used, and the triene intermediate 5b was allowed to stay for 3 days in $CH_2Cl_2$ before cleavage with TFA. Compound 6b was purified by flush chromatography and eluted using 1–4% MeOH in $CH_2Cl_2$ to give 57 mg (48%). For 6b, $^1$H NMR (300 MHz, $CDCl_3$) δ 7.14–7.33 (m, 5H), 6.44 (dt, 1H, J=3.0 Hz, 3.0 Hz, 9.0 Hz), 5.64 (dt, 1H, J=3.0 Hz, 3.0 Hz, 9.0 Hz), 5.20 (d, 1H, J=15.4 Hz), 3.87 (d, 1H, J=15.4 Hz), 3.24 (dd, 1H, J=2 Hz, 10 Hz, H3), 2.82 (t, 1H, J=9.1 Hz, H4), 2.67 (dd, 1H, J=2.0 Hz, 12.7 Hz, H7a), 2.50–2.58 (m, 1H), 2.05–2.19 (m, 2H); $^{13}$C NMR (75 MHz, $CDCl_3$) δ 178.8, 174.1, 136.6, 133.2, 128.7, 127.7, 127.4, 126.8,65.9,46.5,45.7, 44.1, 41.4, 32.9, 26.4, 17.9, 16.9, 16.4; NOESY (400 MHz, $CDCl_3$): between H3 and H4, H3 and H7a, H4 and H7a, H5 and H7a; LC-MS: calcd for $C_{20}H_{26}NO_3$ ($MH^+$) 328, found 328.

Example 2E

Diels-Alder Reaction to Prepare 6c

Freshly prepared 5c from 4a (610 mg, 0.48 mmol) was allowed to stay in $CH_2Cl_2$ for 20 h with occasional swirling. After cleavage with TFA-$CH_2Cl_2$, the mixture was purified with preparative HPLC (Gilson, C-18 column, 10–40% MeCN in water containing 0.1% TFA in 35 min). Compound 6c was the only identified isomer, and was obtained in 64 mg (55% yield). $^1$H NMR (300 MHz, $D_2O$, the solvent peak was set to 4.63 ppm as the reference) δ 7.16–7.28 (m, 5H), 5.59–5.67 (m, 2H), 3.78 (dt, 1H, J=3.6 Hz, 11.1 Hz, 11.1 Hz, H3), 3.35 (dd, 1H, J=3.5 Hz, 14.9 Hz), 3.30 (dd, 1H, J=7.6 Hz, 11.1 Hz), 2.95 (dd, 1H, J=7.0 Hz, 11.3 Hz, H4), 2.67–2.79 (m, 3H), 2.43–2.54 (m, 1H, H7a), 1.88 (q, 1H, J=11.1 Hz, H3a), 0.86 (d, 3H, J=7.3 Hz); $^{13}$C NMR (75 MHz, $D_2O$) δ 179.5, 139.2, 137.0, 131.9, 131.5, 130.2, 124.9, 67.4, 49.1, 49.0, 45.7, 44.7, 39.8, 35.2, 19.5; LC-MS: calcd for $C_{17}H_{22}NO_2$ ($MH^+$) 272, found 272.

Example 2F

Benzoylation and Diels-Alder Reaction to Prepare 6e

The secondary amine 5d after drying under high vacuum over night was treated with a mixture of PhCOCl (10 equiv) and $Et_3N$ in $CH_2Cl_2$ for 2 h to give an intermediate 5e. After filtration and wash with $CH_2Cl_2$ and MeOH, 5e was allowed to stay in $CH_2Cl_2$ for another 16 h. Cleavage of the product gave a crude mixture, whose mass spectrum showed one major peak at 328 (100%) for 6e ($MH^+$), and a peak at 391 as 60% high for an unknown compound. Compound 6e was isolated by column chromatography, eluted using 0.5–1% MeOH in $CH_2Cl_2$, and obtained in 32% yield. $^1$H NMR (300 MHz, $C_6D_6$) δ 7.63 (dd, 2H, J=2.4 Hz, 7.4 Hz), 7.11–7.15 (m, 3H), 5.28–5.38 (m, 2H), 4.52 (d, 1H, J=9.2 Hz, H3), 3.30 (dd, 1H, J=6.3 Hz, 9.6 Hz), 2.89–2.96 (m, 1H), 2.80 (dd, 1H, J=7.1 Hz, 10.3 Hz, H4), 2.67 (dd, 1H, J=10.2 Hz, 11.9 Hz), 2.49–2.54 (m, 1H), 2.05 (q, 1H, J=10.4 Hz, H3a), 1.50–1.70 (m, 1H, H7a), 1.39 (d, 3H, J=7.0 Hz), 1.10 (d, 3H, J=7.2 Hz), 1.05 (d, 3H, J=6.9 Hz); $^{13}$C NMR (75 MHz, $CDCl_3$) δ 178.1, 171.7, 136.7, 134.4, 130.5, 128.3, 128.0, 125.6, 64.7, 54.5, 49.0, 43.9, 43.8, 33.4, 31.5, 21.1, 17.2, 17.0; LC-MS: calcd for $C_{20}H_{26}NO_3$ ($MH^+$) 328, found 328.

Example 2G

Furoylation and Diels-Alder Reaction to Prepare 11a

Resin 4a (250 mg, 0.165 mmol) was treated with a mixture of furoyl chloride (0.2 mL, 2.03 mmol) and $Et_3N$ (0.5 mL) in $CH_2Cl_2$ (6 mL) for 2 h to give 10a. After washing with $CH_2Cl_2$, 10a was allowed to stay in $CH_2Cl_2$ for 60 h with occasional swirling. After cleavage with TFA-$CH_2Cl_2$, the mixture was purified by flash column chromatography and eluted with 0–0.5% MeOH in $CHCl_3$ to give 11a in 34 mg (55%). $^1$H NMR (300 MHz, $CDCl_3$) δ 7.14–7.38 (m, 8H), 6.96 (m, 2H), 6.76 (d, 1H, J=5.9 Hz), 6.32 (dd, 1H, J=1.3 Hz, 5.9 Hz), 5.23 (d, 1H, J=16.0 Hz), 5.19 (dd, 1H, J=1.3 Hz, 6.3 Hz), 4.21 (d, 1H, J=15.4 Hz), 3.54 (ddd, 1H, J=4.2 Hz, 6.4 Hz, 7.3 Hz, H3), 3.29 (dd, 1H, J=4.1 Hz, 13.0 Hz), 2.58 (dd, 1H, J=3.4 Hz, 4.3 Hz, H4), 2.51 (dd, 1H, J=10.5 Hz, 12.7 Hz), 2.32 (dd, 1H, J=3.1 Hz, 7.5 Hz, H3a); $^{13}$C NMR (75 MHz, CDCl$_3$) δ 174.5, 168.0, 135.5, 135.4, 134.9, 134.8, 129.3, 128.9, 128.6, 127.8, 127.7, 127.0, 92.6, 82.7, 63.4, 49.3, 49.1, 44.6, 39.1; NOESY (500 MHz, CDCl$_3$), between H3 and H4, and between H3a and H7; LC-MS: calcd for $C_{23}H_{22}NO_4$ (MH$^+$) 376, found 376.

Example 2F

Furoylation and Diels-Alder Reaction to Prepare 11b

Resin 4b (340 mg, 0.213 mmol) was treated with a mixture of furoyl chloride (0.25 mL, 2.53 mmol) and Et$_3$N (0.8 mL) in CH$_2$Cl$_2$ (8 mL) for 2 h to give 10b. After washing with CH$_2$Cl$_2$, 10b was allowed to stay in CH$_2$Cl$_2$ for 7 days with occasional swirling. After cleavage with TFA-CH$_2$Cl$_2$, the mixture was purified by flash column chromatography and eluted with 0–2% MeOH in CHCl$_3$ to give lib in 36 mg (52%). $^1$H NMR (300 MHz, CDCl$_3$) δ 7.18–7.34 (m, 5H), 6.80 (d, 1H, J=5.9 Hz, H7), 6.46 (dd, 1H, J=1.6 Hz, 5.9 Hz, H6), 5.37 (dd, 1H, J=.1.3 Hz, 4.5 Hz), 5.28 (d, 1H, J=15.2 Hz), 3.83 (d, 1H, J=15.2 Hz), 3.31 (dd, 1H, J=3.7 Hz, 7.9 Hz, H3), 3.16 (dd, 1H, J=3.7 Hz, 4.2 Hz, H4), 2.37 (dd, 1H, J=3.2 Hz, 7.8 Hz, H3a), 2.10–2.00 (m, 1H), 0.86 (d, 3H, J=5.3 Hz), 0.84 (d, 3H, J=5.2 Hz); $^{13}$C NMR (75 MHz, CDCl$_3$) δ 174.6, 168.6, 135.3, 135.24, 135.21, 128.8, 127.7, 127.6, 92.7, 82.3, 65.9, 50.6, 44.1, 42.1, 26.4, 18.1, 14.3; NOESY (400 MHz, CDCl$_3$), between H3 and H4, weak between H3a and H7; LC-MS: calcd for $C_{19}H_{22}NO_4$ (MH$^+$) 328, found 328.

Example 2G

Benzoylation and Diels-Alder Reaction to Prepare 11c

After following the benzoylation procedure for 6e, the Diels-Alder reaction of 10c was allowed for 60 h in CH$_2$Cl$_2$. Compound 11c was obtained in 65% yield after flush column chromatography (eluted with 0–1% MeOH in CH$_2$Cl$_2$). $^1$H NMR (300 MHz, CDCl$_3$) δ 7.36–7.53 (m, 5H), 6.44 (d, 1H, J=5.8 Hz), 6.36 (dd, 1H, J=1.1 Hz, 5.9 Hz), 5.23 (d, 1H, J=4.2 Hz), 4.14 (dd, 1H, J=5.1 Hz, 7.0 Hz), 3.93 (d, 1H, J=12.8 Hz), 3.88 (d, 1H, J=12.7 Hz), 3.21 (dd, 1H, J=3.2 Hz, 4.3 Hz), 2.60–2.69 (m, 1H), 2.40 (dd, 1H, J=3.0 Hz, 7.1 Hz), 0.98 (d, 6H, J=6.8 Hz); $^{13}$C NMR (75 MHz, CDCl$_3$) δ 174.6, 171.0, 136.7, 135.3, 135.1, 130.3, 128.4, 127.5, 95.3, 80.6, 67.6, 52.6, 46.5, 29.2, 18.8, 15.9; NOESY (400 MHz, CDCl$_3$), between H1a and H3, between Hie and H3a, between H1e and H7, between H3 and H4, weak between H3a and H7; LC-MS: calcd for $Cl_9H_{22}NO_4$ (MH$^+$) 328, found 328.

Example 2H

Diels-Alder Reaction to Prepare 11d

Freshly prepared 10d from 2a (268 mg, 0.168) mmol) was allowed to stay in CH$_2$Cl$_2$ for 4 days with occasional swirling. After cleavage with TFA—CH$_2$Cl$_2$, $^1$H NMR of the crude mixture showed two isomers in a ratio of 2:1. Only the major isomer was made pure using preparative HPLC (Gilson, C-18 column, 1–7% MeCN in water containing 0.1% TFA in 30 min) to give 16 mg (32% yield). $^1$H NMR (300 MHz, CD$_3$OD) δ 7.26–7.35 (m, 5H), 6.64 (d, 1H, J=5.7 Hz), 6.35 (d, 1H, J=5.7 Hz), 4.13 (d, 1H, J=12.7 Hz), 4.08 (d, 1H, J=12.7 Hz), 3.96 (d, 1H, J=13.7 Hz), 3.64–3.72 (m, 1H), 3.53 (d, 1H, J=13.7 Hz), 3.10–3.19 (m, 2H), 2.89 (d, 1H, J=2.9 Hz), 2.61 (dd, 1H, J=2.8 Hz, 10.5 Hz, H3a); $^{13}$C NMR (75 MHz, CDCl$_3$) δ 173.0, 137.5, 136.9, 136.6, 130.2, 128.6, 96.4, 67.4, 61.2, 56.2, 50.2, 47.3, 38.2; NOESY (500 MHz, CDCl$_3$), between H1a and H3, between H1e and H3a, between H1e and H7, between H3 and H4, and between H3a and H7; LC-MS: calcd for $C_{17}H_{20}NO_4$ (MH$^+$) 302, found 302.

Example 2I

Diels-Alder Reaction to Prepare 13

Freshly prepared 12 from 3a (180 mg, 0.126) mmol) was allowed to stay in CH$_2$Cl$_2$ for 48 h with occasional swirling. After cleavage with TFA-CH$_2$Cl$_2$, $^1$H NMR and MS of the crude mixture showed partial di-alkylation during the preparation of 12. The major product was made pure using preparative HPLC (Gilson, C-18 column, 10–55% MeCN in water containing 0.1% TFA in 30 min) to give 14 mg (37% yield). $^1$H NMR (300 MHz, CD$_3$OD) δ 7.28–7.43 (m, 6H), 6.35 (d, 1H, J=1.9 Hz), 3.82 (dt, 1H, J=2.6 Hz, 10.7 Hz, 10.7 Hz, H3), 3.68 (d, 1H, J=9.5 Hz, H4),3.51 (dd, 1H, J=7.2 Hz, 11.4 Hz), 3.26 (dd, 1H, J=3.0 Hz, 15.1 Hz), 3.11 (t, 1H, J=11.0 Hz), 2.95 (dd, 1H, J=3.3 Hz, 15.0 Hz), 2.86 (dd, 1H, J=11.5 Hz, 15.1 Hz), 2.48–2.63 (m, 2H), 2.41 (q, 1H, J=10.5 Hz, H3a); $^{13}$C NMR (75 MHz, CD$_3$OD) δ 175.9, 151.0, 143.7, 137.4, 130.3, 129.8, 128.7, 117.1, 110.3, 66.1, 48.5, 43.7, 41.4, 38.1, 27.2; LC-MS: calcd for $C_{18}H_{20}NO_3$ (MH$^+$) 297, found 297.

Example 2J

Coupling Acylation and Diels-Alder Reaction to Prepare 15

The secondary amine 4b (350 mg, 0.24 mmol) after drying under high vacuum over night was treated with a mixture of trans-3-fuiranacrylic acid (167 mg, 1.21 mmol), DIEA (0.5 mL), and HATU (460 mg, 1.21 mmol) in CH$_2$Cl$_1$ (8 mL) for 2 h. This coupling procedure was repeated two more times to give an intermediate 5e. After filtration and wash with CH$_2$Cl$_2$ and MeOH, 5e was allowed to stay in CH$_2$Cl$_2$ for another 4 days. Cleavage of the product gave a crude mixture containing the major product 15, which was isolated by column chromatography, eluted using 0–0.5% MeOH in CH$_2$Cl$_2$, and obtained in 31mg (37% yield). $^1$H NMR (300 MHz, C,D,) δ 6.95–7.12 (m, 6H), 5.89 (d, 1H, J=1.9 Hz), 5.23 (d, 1H, J=15.5 Hz), 3.64 (d, 1H, J=15.4 Hz), 3.29 (d, 1H, J=9.8 Hz, H4), 2.97 (dd, 1H, J=1.6 Hz, 11.3 Hz, H3), 2.92 (ddd, 1H, J=1.8 Hz, 5.1 Hz, 15.5 Hz), 2.22 (dt,1H, J=9.7 Hz, 9.7 Hz, 12.6 Hz, H3a), 2.41 (ddd, 1H, J=2.6 Hz, 11.9 Hz, 15.4 Hz). 1.86–1.99 (m, 2H), 0.76 (d, 3H, J=7.3 Hz), 0.75 (d, 3H, J=7.1 Hz); $^{13}$C NMR (75 MHz, $C_6D_6$) δ 175.3, 174.9, 146.1, 142.8, 136.2, 128.7, 127.6, 127.5, 119.5, 110.8, 65.6, 46.0, 44.9, 44.4, 40.8, 26.8, 21.8, 17.2, 17.0; LC-MS: calcd for $C_{21}H_{24}NO_4$ (MH$^+$) 354, found 354.

We claim:

1. A method for synthesing compounds having an hexahydroisoindole or hexahydroisooxyindole moiety selected from those moieties of the formulae:

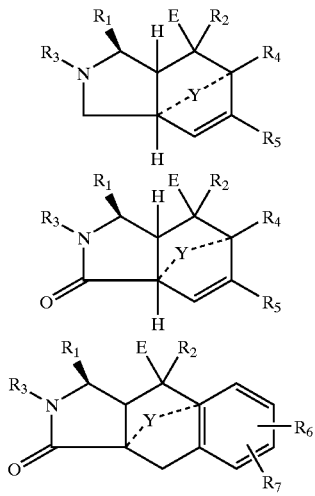

wherein $R_1$ is a standard natural amino acid side chain other than that derived from glycine; $R_2$ is H, $CH_3$, COOR or CN; $R_3$ is H, alkyl, substituted alkyl, aryl, substituted aryl, butoxycarbonyl (BOC), or carbobenzyloxy (CBz); $R_4$ and $R_5$ are the same or different and are H, benzyl and COOR or $R_4$ and $R_5$ together form an aryl, substituted aryl, cycloalkyl or a heterocyclic ring; $R_6$ and $R_7$ are the same or different and are H, alkyl, halo or alkoxy; R is H, lower alkyl, or benzyl; Y is absent, an oxygen or a $CH_2$ bridging group; P is a solid support resin; and E is COOP; said method comprising:

a) preparing a compound comprising a triene moiety selected from those of the formula and stereochemistry:

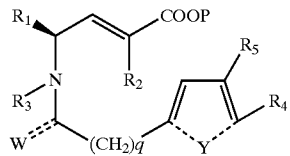

by (i) reacting a protected amino aldehyde (1) with a dialkyl α-phosphonoester (2) to generate a protected amine (3)

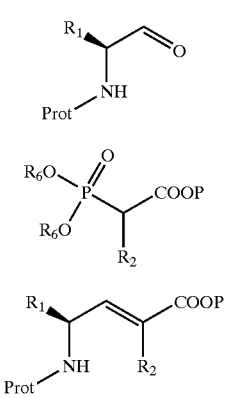

(ii) removing the protecting group from the amine (3) and alkylating the resulting intermediate to generate (4)

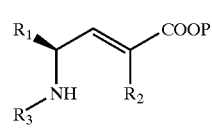

and (iii) reacting (4) with an acid halide, anhydride or aldehyde (5)

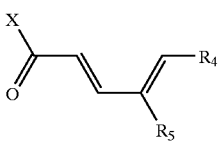

wherein Prot is a standard amino acid protecting group, wherein $R_6$ is lower alkyl, wherein X is a chlorine atom, a bromine atom, $R_7C(O)$— wherein $R_7$ is lower alkyl, or H, and wherein W is oxygen or is absent; q is zero; Y is an oxygen, a $CH_2$ bridging group or is hydrogen at each carbon atom; and $R_1$ to $R_5$ and P are as recited above; and b) converting said triene moiety to the corresponding hexahydroisoindole or hexahydroisooxyindole moiety by a Diels Alder cycloaddition reaction at a temperature of between 0 and 110° C. and a reaction time of 1 to 64 hours.

2. The method according to claim 1 wherein $R_1$ is a standard natural amino acid side chain other than that derived from glycine;

$R_2$ is H, $CH_3$, COOR or CN; $R_3$ is H, benzyl, substituted benzyl, butoxycarbonyl (BOC) or carbobenzyloxy (CBz), $R_4$ and $R_5$ are the same or different and are H, benzyl, or COOR, taken together form a saturated carbocyclic ring of 5–6 ring atoms, taken together form an unsaturated carbocyclic ring of 5–6 ring atoms, taken together form a saturated heterocyclic ring having 5–6 ring atoms, or taken together form an unsaturated heterocyclic ring having 5–6 ring atoms, wherein said heterocyclic rings have 1,2 or 3 atoms selected from the group consisting of nitrogen, oxygen and sulfur;

R is H, lower alkyl, or benzyl; and

X is absent, oxygen or a $CH_2$ bridging group.

3. The method according to claim 1 wherein $R_1$ is a standard natural amino acid side chain other than that derived from glycine; $R_2$ is H, $CH_3$, COOR or CN; $R_3$ is H, benzyl, butoxycarbonyl (BOC) or carbobenzyloxy (CBz), $R_4$ and $R_5$ are the same or different and are H, benzyl, COOR, taken together form a saturated carbocyclic ring of 5 or 6 ring atoms, taken together form an unsaturated carbocyclic ring of 5 or 6 ring atoms, or taken together form a furan ring; R is H, lower alkyl, or benzyl; and X is absent.

4. A method for synthesing a plurality of reduced isoindole or isooxyindole compounds covalently attached to a solid support said method comprising:

a) preparing a solid support comprising at least one compound attached thereto which compound comprises a triene moiety selected from those of the formula and stereochemistry:

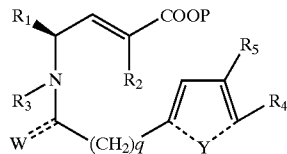

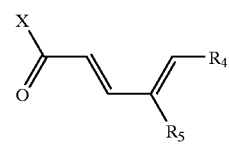

wherein $R_1$ is a standard natural amino acid side chain other than that derived from glycine; $R_2$ is H, $CH_3$, COOR or CN; $R_3$ is H, alkyl, substituted alkyl, aryl, substituted aryl, butoxycarbonyl (BOC), carbobenzyloxy (CBz), $R_4$ and $R_5$ are the same or different and are selected from H, benzyl and COOR or $R_4$ and $R_5$ together form an aryl, substituted aryl, cycloalkyl or a heterocyclic ring; R is selected from H, lower alkyl, or benzyl, Y is absent or is an oxygen or $CH_2$ bridging group, P is a solid support resin, and q is zero by (i) reacting a protected amino aldehyde (1) with a dialkyl α-phosphonoester (2) to generate a protected amine (3)

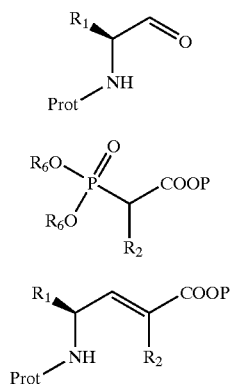

(ii) removing the protecting group from the amine (3) and alkylating the resulting intermediate to generate (4)

and (iii) reacting (4) with an acid halide, anhydride or aldehyde (5)

wherein Prot is a standard amino acid protecting group, wherein $R_6$ is lower alkyl, wherein X is a chlorine atom, a bromine atom, $R_7C(O)$— wherein $R_7$ is lower alkyl, or H, and wherein W is oxygen or is absent; q is zero; Y is an oxygen, a $CH_2$ bridging group or is hydrogen at each carbon atom; and $R_1$ to $R_5$ and P are as recited above; and b) converting said triene moiety at a temperature of between 0 and 110° C. and a reaction time of 1 to 64 hours to a corresponding hexahydroisoindole or hexahydroisooxyindole moiety of a formula selected the group consisting of

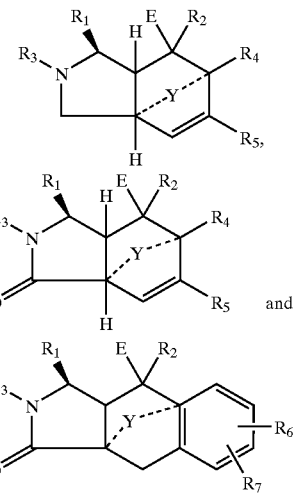

by a Diels Alder cycloaddition reaction.

5. The method according to claim 1 wherein Prot is Fmoc or Boc, $R_6$ is ethyl, X is a chlorine atom or $R_7C(O)$—, and $R_7$ is isobutyl.

6. The method according to claim 2 wherein Prot is Fmoc or Boc, $R_6$ is ethyl, X is a chlorine atom or $R_7C(O)$—, and $R_7$ is isobutyl.

7. The method according to claim 3 wherein Prot is Fmoc or Boc, $R_6$ is ethyl, X is a chlorine atom or $R_7C(O)$—, and $R_7$ is isobutyl.

8. The method according to claim 4 wherein Prot is Fmoc or Boc, $R_6$ is ethyl, X is a chlorine atom or $R_7C(O)$—, and $R_7$ is isobutyl.

* * * * *